(12) United States Patent
Sun et al.

(10) Patent No.: US 9,575,032 B2
(45) Date of Patent: Feb. 21, 2017

(54) METHOD OF ANALYZING AT LEAST TWO INHIBITORS SIMULTANEOUSLY IN A PLATING BATH

(71) Applicant: Hong Kong Applied Science and Technology Research Institute Company Limited, Hong Kong (HK)

(72) Inventors: Yaofeng Sun, Hong Kong (HK); Minghui Gao, Hong Kong (HK); Hai Xia, Hong Kong (HK)

(73) Assignee: Hong Kong Applied Science and Technology Research Institute Company Limited, Hong Kong Science Park, Shatin, New Territories, Hong Kong (CN)

( * ) Notice: Subject to any disclaimer, the term of this patent is extended or adjusted under 35 U.S.C. 154(b) by 341 days.

(21) Appl. No.: 14/453,636

(22) Filed: Aug. 7, 2014

(65) Prior Publication Data

US 2016/0041125 A1    Feb. 11, 2016

(51) Int. Cl.
*G01N 27/26* (2006.01)
*G01N 27/48* (2006.01)
*C25D 21/12* (2006.01)
*C25D 21/14* (2006.01)
*C25D 21/18* (2006.01)

(52) U.S. Cl.
CPC .............. *G01N 27/48* (2013.01); *C25D 21/12* (2013.01); *C25D 21/14* (2013.01); *C25D 21/18* (2013.01); *G01N 27/26* (2013.01)

(58) Field of Classification Search
CPC ........ C25D 21/12; C25D 21/14; C25D 21/16; G01N 27/48
See application file for complete search history.

(56) References Cited

U.S. PATENT DOCUMENTS

| | | | |
|---|---|---|---|
| 6,495,011 B2 * | 12/2002 | Robertson | G01N 27/42 204/434 |
| 6,572,753 B2 | 6/2003 | Chalyt et al. | |
| 6,808,611 B2 | 10/2004 | Sun et al. | |
| 7,186,326 B2 | 3/2007 | Shalyt et al. | |
| 7,384,535 B2 | 6/2008 | Sonnenberg et al. | |
| 2013/0161203 A1 * | 6/2013 | Mayer | C25D 21/14 205/775 |

* cited by examiner

Primary Examiner — Nicholas A Smith
Assistant Examiner — Brian W Cohen
(74) Attorney, Agent, or Firm — Daniel R. Collopy

(57) ABSTRACT

The presently claimed invention provides an accurate, fast, and cost effective method for determining the additive concentrations of at least two inhibitors simultaneously in an electroplating bath by using different electrical load conditions. The method of the present invention is able to determine additive concentrations of different inhibitors effectively during on-line feedback control for adjusting the amount of additives in the electroplating bath to maintain the additive concentrations within pre-defined limits during device production.

8 Claims, 13 Drawing Sheets

METHOD OF ANALYZING AT LEAST TWO INHIBITORS SIMULTANEOUSLY IN A PLATING BATH

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to a method of analyzing additives in an electroplating bath. More particularly, the present invention relates to a method of analyzing at least two inhibitors simultaneously in an electroplating bath.

BACKGROUND

Electrodeposition is a frequently-used method to deposit different conductive metals into vias for forming electrical connections. Electroplating baths for electrodeposition of metal are typically aqueous solutions comprising metal salts, ionic electrolytes, and myriad additives like accelerators (brighteners), suppressors levelers, etc. The additives play key roles in electrodeposition since inappropriate species or concentrations may lead to voids, insufficient filling, and non-uniform deposit, and such defects can generate adverse effects to the devices, leading to great loss during mass production. For example, FIG. 1A-B show a via with poor filling quality at inappropriate leveler concentration, and another via with good filing quality at appropriate leveler concentration respectively.

As electrodeposition is commonly used for fabrication of electronic components and devices, reliable operation of electroplating baths in a manufacturing process need employ suitable analytical methods for determining the appropriate concentrations of the additives. These analytical methods are often used to determine the concentrations of species in the bath during operation, so as to provide on-line feedback control, and adjust the amount of additive for maintaining concentrations within pre-determined limits as shown in FIG. 2.

U.S. Pat. No. 6,572,753 provides a method for analysis of three organic additives in an acid copper plating bath. Cyclic voltammetric stripping (CVS) methods are used to measure the concentrations of the suppressor and anti-suppressor based on the effects of these additives on the copper electrodeposition rate. The method uses measurements of the copper electrodeposition rate to determine the concentration of the leveler additive. The other two additives are included in the measurement solution at concentrations determined to provide the optimum compromise between minimal interference, high sensitivity and good reproducibility for the leveler analysis. Nevertheless, the method provides only a single analysis for leveler.

U.S. Pat. No. 6,808,611 discloses an electro-analytical method for determining the concentration of an organic additive in an acidic or basic metal plating bath using an organic chemical analyzer. The method includes preparing a supporting-electrolyte solution, preparing a testing solution including the supporting-electrolyte solution and a standard solution, measuring an electrochemical response of the supporting-electrolyte solution using the organic chemical analyzer, and implementing an electro-analytical technique to determine the concentration of the organic additive in the plating bath from the electrochemical response measurements. However, the method provides merely a single analysis for leveler.

U.S. Pat. No. 7,186,326 discloses a method for measuring the concentrations of a suppressor additive and an anti-suppressor additive in a plating bath for electrodeposition of a metal. Suppressor and anti-suppressor additives in an acid copper sulfate plating bath are analyzed by the cyclic voltammetric stripping method without cleaning or rinsing the cell between the two analyses. The suppressor analysis is performed first and the suppressor concentration in the resulting measurement solution is adjusted to a predetermined value corresponding to full suppression. This fully-suppressed solution is then used as the background electrolyte for the anti-suppressor analysis. However, the method provides only a sequential analysis for suppressor and accelerator.

U.S. Pat. No. 7,384,535 provides a method for determining the quantity of both brightener and leveler in a metal plating bath. The method is able to improve the reproducibility of measuring brighteners and levelers in electroplating baths. Nevertheless, the method provides just an integrated analysis for accelerator and leveler.

In actual mass production, two or more inhibitors such as a leveler and suppressor are frequently employed simultaneously in recipes for acquiring good via filling quality. However, the abovementioned methods fail to provide an integrated analysis for two or more inhibitors simultaneously. The problem raised here is that the sum of concentrations of at least two inhibitors is not equivalent to the measured concentration since the inhibitors provide other inhibiting effects when different inhibitors are mixed in a plating solution. For example, according to the prior art, when simply considering the equivalent concentration of two inhibitors by the sum of concentrations of each inhibitors, such calculation fails to provide the same results as the measured inhibitor concentration during the mass production, thereby leading to error occurred as shown in Table 1:

TABLE 1

| Sample | Actual S concentration | Meas. S concentration | Error |
|---|---|---|---|
| 1 | 8 ml/L | 11.5 ml/L | 43.91% |
| 2 | 5 ml/L | 6.59 ml/L | 38.13% |

As shown in Table 1, the error generated can be as large as to be 43%. Such shortcoming makes manufacturer incapable of maintaining the appropriate additive concentration during the mass production, thereby substantially lowering the yield of products.

Therefore, there is an unmet need to provide an accurate, fast, and cost effective method for determining the concentrations of at least two inhibitors simultaneously in an electroplating bath during on-line feedback control for appropriate adjustment of the amount of additives in the bath to maintain the additive concentrations within pre-defined limits during device production.

SUMMARY

Accordingly, it is a first aspect of the presently claimed invention to provide a method of analyzing at least two inhibitors simultaneously in a plating bath using different electrical load approaches.

In accordance with an embodiment of the presently claimed invention, a method for determining additive concentrations of at least two inhibitors in a plating bath comprises: determining at least two inhibition factors of the at least two inhibitors by applying at least two electrical load conditions on at least two supporting solution respectively; determining equivalent suppressor concentrations of a testing solution under the at least two electrical load conditions respectively, wherein the testing solution comprises a virgin make-up solution and a portion of the plating bath, and the virgin make-up solution is an electrolyte solution comprising substances of the plating except the at least two inhibitors; and determining the additive concentrations of the at least two inhibitors based on the at least two inhibition factors and the equivalent suppressor concentrations of the testing solution under the at least two electrical load conditions.

In accordance with an embodiment of the presently claimed invention, the step of determining the at least two inhibition factors further comprises steps of:
(a) providing a first standard solution of a first inhibitor from the at least two inhibitors, having a known amount of the first inhibitor;
(b) providing the virgin make-up solution;
(c) measuring an original deposition rate ($R_0$) of the virgin make-up solution under a first electrical load condition from one of the at least two electrical load conditions;
(d) adding a first volume of the first standard solution of the first inhibitor into the virgin make-up solution to form the supporting solution comprising the first volume of the first standard solution of the first inhibitor;
(e) measuring a first deposition rate ($R_1$) of the supporting solution comprising the first volume of the first standard solution of the first inhibitor under the first electrical load condition to determine a first deposition rate ratio calculated by $R_1/R_0$;
(f) repeating the steps (d)-(e) by adding another volume of the first standard solution of the first inhibitor to determine another deposition rate ratio till obtaining a calibration curve of the first inhibitor;
(g) repeating the steps (a)-(f) by using another standard solution of another inhibitor from the at least two inhibitors to obtain another calibration curve of the another inhibitor till obtaining all of the calibration curves of each of the at least two inhibitors;
(h) determining calibrated concentrations of the at least two inhibitors for the first electrical load condition at a predetermined value of the deposition rate ratio based on the calibration curves of each of the at least two inhibitors;
(i) repeating the steps (a)-(g) under another electrical load condition from the at least two electrical load conditions and determining another calibrated concentrations of another inhibitor for another electrical load condition at the predetermined value of the deposition rate ratio till obtaining all of the calibrated concentrations of each of the at least two inhibitors for each of the at least two electrical load conditions; and
(j) determining the at least two inhibition factors for each of the at least two electrical load conditions based on all of the calibrated concentrations.

In accordance with an embodiment of the presently claimed invention, the step of determining the equivalent suppressor concentrations of the testing solution further comprises steps of:
(a) providing a volume of the virgin mark-up solution;
(b) measuring an original deposition rate of the volume of the virgin mark-up solution ($R_0'$) under the first electrical load condition;
(c) adding a first volume of the plating bath into the virgin mark-up solution to form the testing solution comprising the first volume of the plating bath;
(d) measuring a first deposition rate ($R_1'$) of the testing solution comprising the first volume of the plating bath under the first electrical load condition to determine a first deposition rate ratio calculated by $R_1'/R_0'$;
(e) repeating the steps (c)-(d) by adding another volume of the plating bath to determine another deposition rate ratio till obtaining an analysis curve of the plating bath solution for the first electrical load condition;
(f) determining a volume of plating bath sample addition at the predetermined value of the deposition rate ratio for the first electrical load condition;
(g) repeating steps (a)-(e) under another electrical load condition from the at least two electrical load conditions and determining another volume of plating bath sample addition for another electrical load condition at the predetermined value of the deposition rate ratio till obtaining all of the volumes of plating bath sample addition for each of the at least two electrical load conditions; and
(h) determining the equivalent suppressor concentrations of the plating bath solution based on the volumes of plating bath sample addition of each of the at least two electrical load conditions, and the calibrated concentrations of each of the at least two electrical load conditions.

A second aspect of the presently claimed invention is to provide a computer-readable medium whose contents cause a computing system to perform the methods of the present invention.

The presently claimed invention provides an accurate, fast, and cost effective method for determining the concentrations of at least two inhibitors simultaneously in an electroplating bath during on-line feedback control for appropriate adjustment of the amount of additives to maintain the inhibitor concentrations within pre-defined limits during device production.

BRIEF DESCRIPTION OF THE DRAWINGS

Embodiments of the present invention are described in more detail hereinafter with reference to the drawings, in which.

DETAILED DESCRIPTION

In the following description, methods for analyzing at least two inhibitors simultaneously in a plating bath using different electrical load conditions are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

As used herein, the term "inhibitor" refers to an additive for electroplating, which reduces deposition rate during electroplating.

As used herein, the term "inhibition factor" refers to a concentration ratio of two inhibitors when achieving the same inhibition effect on electroplating rate.

As used herein, the term "equivalent suppressor (S) concentration" refers to a nominal concentration value for mixed inhibitors equivalent to one of the mixed inhibitors. Such that various inhibitor concentrations are transferred into one equivalent S concentration.

Figure 1A:
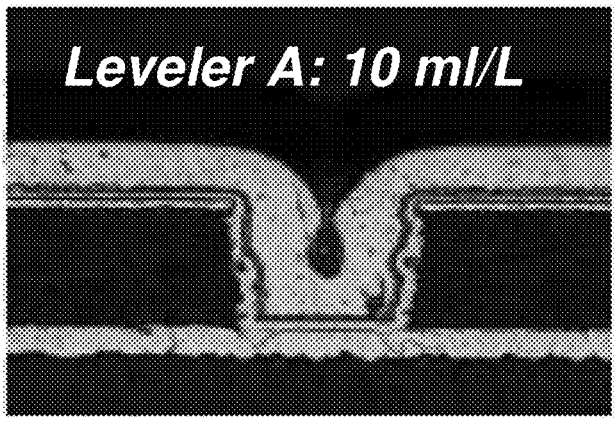
FIG. 1A-B show two photos of a via with poor filling quality at inappropriate leveler concentration, and another via with good filing quality at appropriate leveler concentration respectively.
Figure 1B:
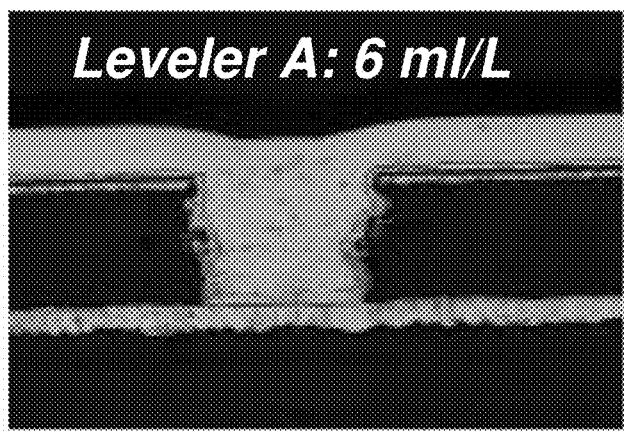
Figure 2:
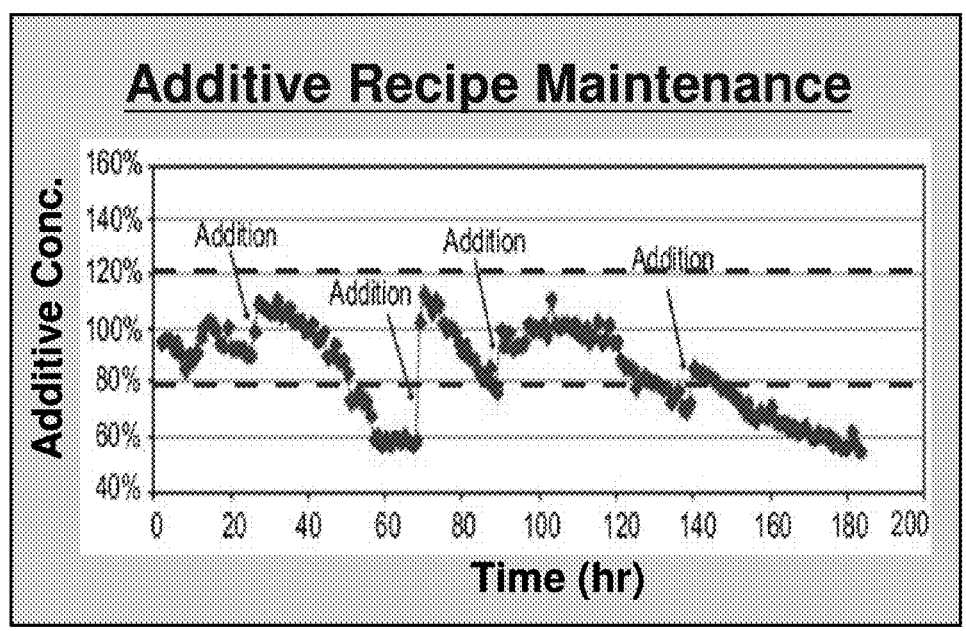
FIG. 2 is a graph showing additive concentrations monitored with time during mass production for maintaining appropriate additive recipe within a control limit.
Figure 3:
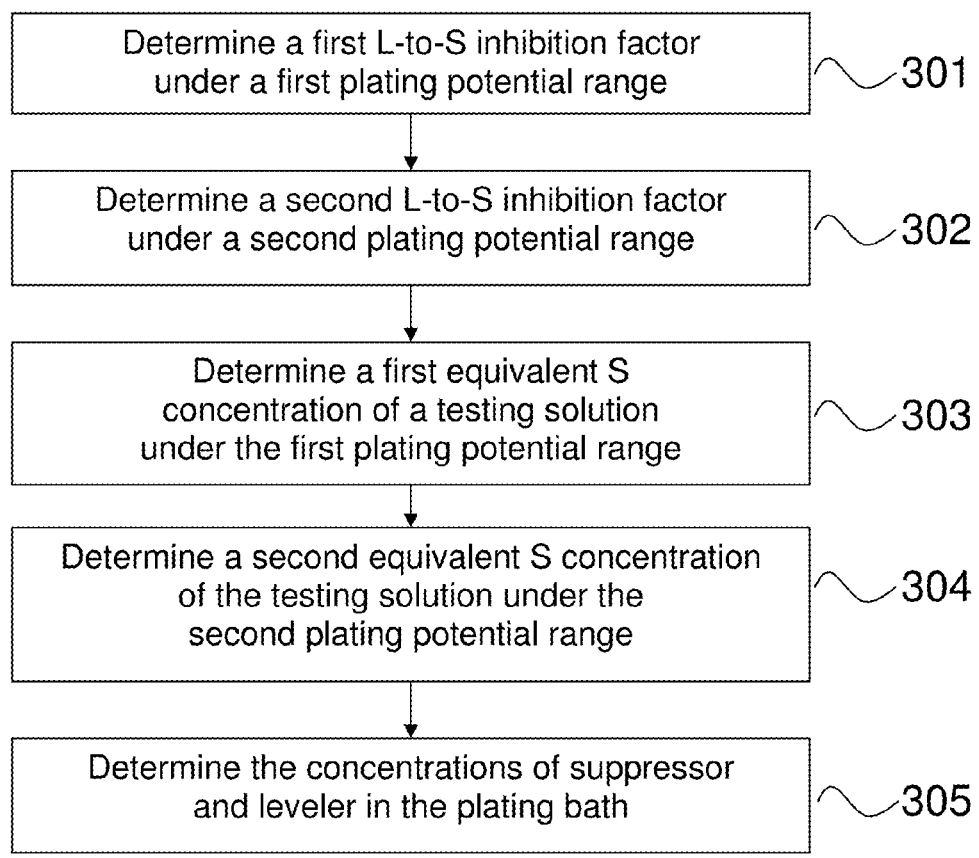
FIG. 3 shows a process flow chart illustrating the steps of a method for analyzing two inhibitors simultaneously in a plating bath using two different potential range approach according to one embodiment of the presently claimed invention.

FIG. 3 shows a process flow chart illustrating the steps of a method for analyzing two inhibitors simultaneously in a plating bath using two different potential ranges according to one embodiment of the presently claimed invention. The inhibitors are a leveler, L and a suppressor, S. In step 301, a first L-to-S inhibition factor, α under a first plating potential range is determined. In step 302, a second L-to-S inhibition factor, β is determined under a second plating potential range. In step 303, a first equivalent suppressor concentration, $\gamma_{p1}$ of a testing solution under the first plating potential range is determined. In step 304, a second equivalent suppressor concentration, $\gamma_{p2}$ of the testing solution under the second plating potential range is determined. In step 305, a suppressor concentration, $C_S$ and a leveler concentration, $C_L$ in the plating bath are determined based on the first L-to-S inhibition factor, the second L-to-S inhibition factor, the first equivalent suppressor concentration, and the second equivalent suppressor concentration.

Accordingly, the suppressor concentration, $C_S$ and the leveler concentration, $C_L$ are calculated as follows:

$$C_S + \alpha C_L = \gamma_{p1} \tag{1}$$

$$C_S + \beta C_L = \gamma_{p2} \tag{2}$$

Hence, there are:

$$C_L = \frac{\gamma_{p1} - \gamma_{p2}}{\alpha - \beta} \tag{3}$$

$$C_S = \frac{\alpha \gamma_{p1} - \beta \gamma_{p2}}{\alpha - \beta} \tag{4}$$

Figure 4:
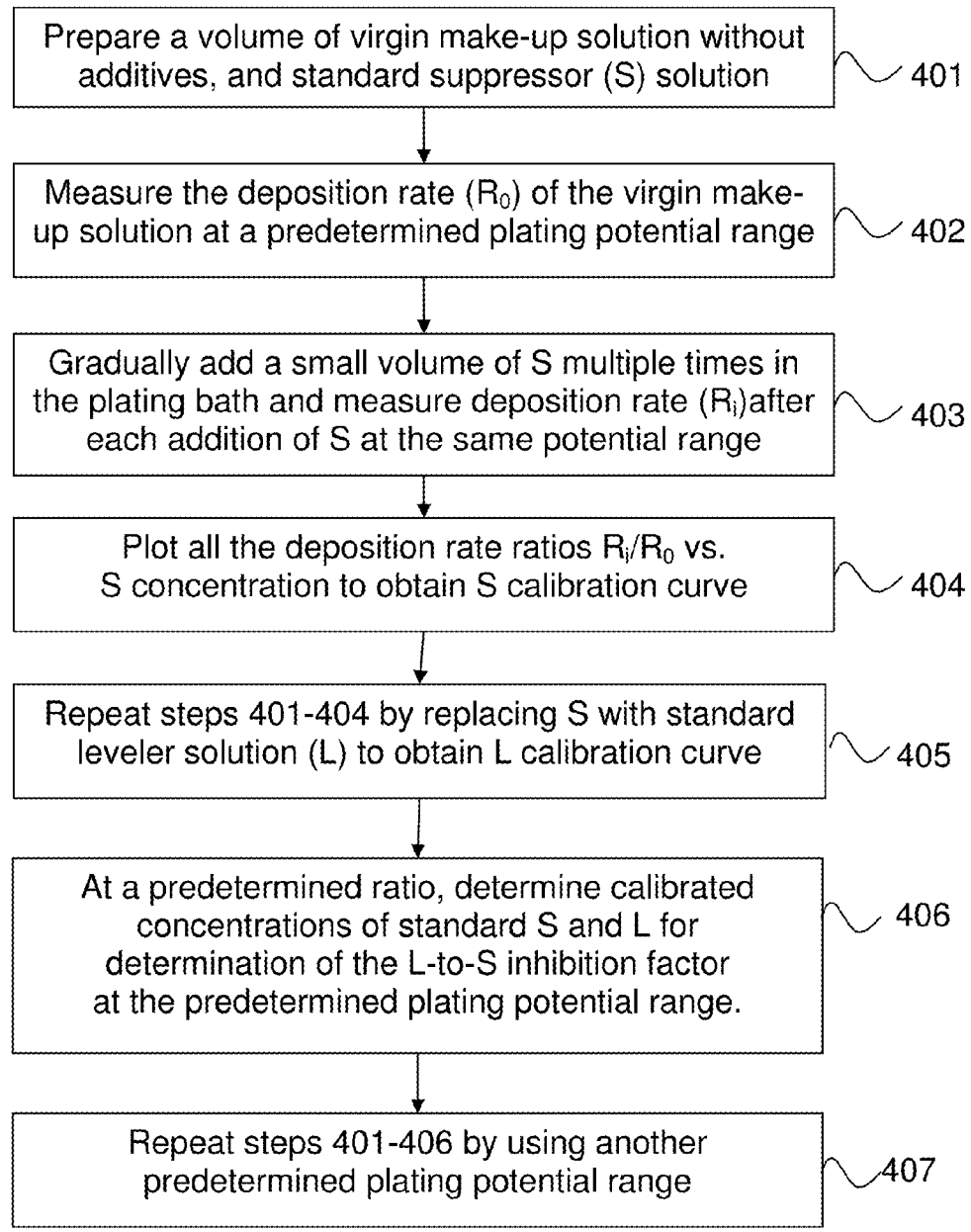
FIG. 4 shows a process flow chart illustrating the steps of determining two inhibition factors under two different plating potential ranges according to one embodiment of the presently claimed invention.

FIG. 4 shows a process flow chart illustrating the steps of determining the first and the second L-to-S inhibition factors under two different plating potential ranges according to one embodiment of the presently claimed invention. In step 401, a volume of virgin make-up solution without additives and standard suppressor solution are prepared. The virgin make-up solution comprises all inorganic substance of the plating bath except the first and the second inhibitors, and the standard suppressor solution has a known concentration of the suppressor. In step 402, the deposition rate ($R_0$) of the virgin make-up solution at a predetermined plating potential range is measured. In step 403, a small volume of the standard suppressor solution is gradually added into the virgin make-up solution in multiple times to form multiple supporting solutions, and various deposition rates ($R_i$) of the supporting solutions having different volumes of the standard suppressor solutions are measured after each addition of the standard suppressor solution at the same plating potential range. In step 404, all deposition rate ratios, calculated by $R_i/R_0$, are plotted versus the suppressor concentration to obtain a suppressor calibration curve. In step 405, steps 401-404 are repeated by replacing the standard suppressor solution with a standard leveler solution to obtain a leveler calibration curve. In step 406, at a predetermined deposition rate ratio, calibrated concentrations of the standard suppressor solution ($C_S^{cali}$) and the standard leveler solution ($C_L^{cali}$) are determined based on the suppressor and the leveler calibration curves for further determination of the L-to-S inhibition factor (α or β) at the predetermined plating potential range. In step 407, steps 401-406 are repeated with another predetermined plating potential range to determine calibrated concentrations at another predetermined plating potential range.

Accordingly, the L-to-S inhibition factors for a first and a second plating potential ranges, α and β are calculated as follow:

$$\alpha = \frac{C_{S,p1}^{cali}}{C_{L,p1}^{cali}} \tag{5}$$

$$\beta = \frac{C_{S,p2}^{cali}}{C_{L,p2}^{cali}} \qquad (6)$$

where $C_{S,p1}^{cali}$ is the calibrated concentration of the suppressor at the first plating potential range, $C_{L,p1}^{cali}$ is the calibrated concentration of the leveler at the first plating potential range, S,p2$^{cali}$ is the calibrated concentration of the suppressor at the second plating potential range, and $C_{L,p2}^{cali}$ is the calibrated concentration of the leveler at the second plating potential range.

According to an embodiment of the presently claimed invention, cyclic voltammetric stripping is used to apply different plating potential ranges, and measure the deposition rates for both of the virgin make-up solution and the supporting solutions with addition of different volumes of the inhibitors. Cyclic voltammetric stripping is an electrochemical technique commonly used for the measurement of organic additives in a plating bath. It is based on the effect that the additives have on the rate of electroplating. Regardless of the specific type of organic additive such as brightener, leveler, or grain refiner, the activity of the organic additive is reflected in the change of the plating rate. The analysis is conducted in an electrochemical cell using a three-electrode system, one of which is a platinum rotating disk electrode. During measurement, the potential of the platinum electrode is controlled by the instrument. The potential is scanned at a constant rate back and forth between negative and positive voltage limits. A small amount of metal from the plating bath is alternatively plated onto and stripped off the working electrode as the potential is changed. During the scan, the current at the working electrode is measured as a function of potential. As the activity of the additive affects the plating rate of the metal onto the electrode, the plating rate is determined by calculating the charge required to strip the metal off the working electrode. The relationship between the stripping charge and the activity of the additives is used to quantitatively measure the additives and their components.

Figure 5:
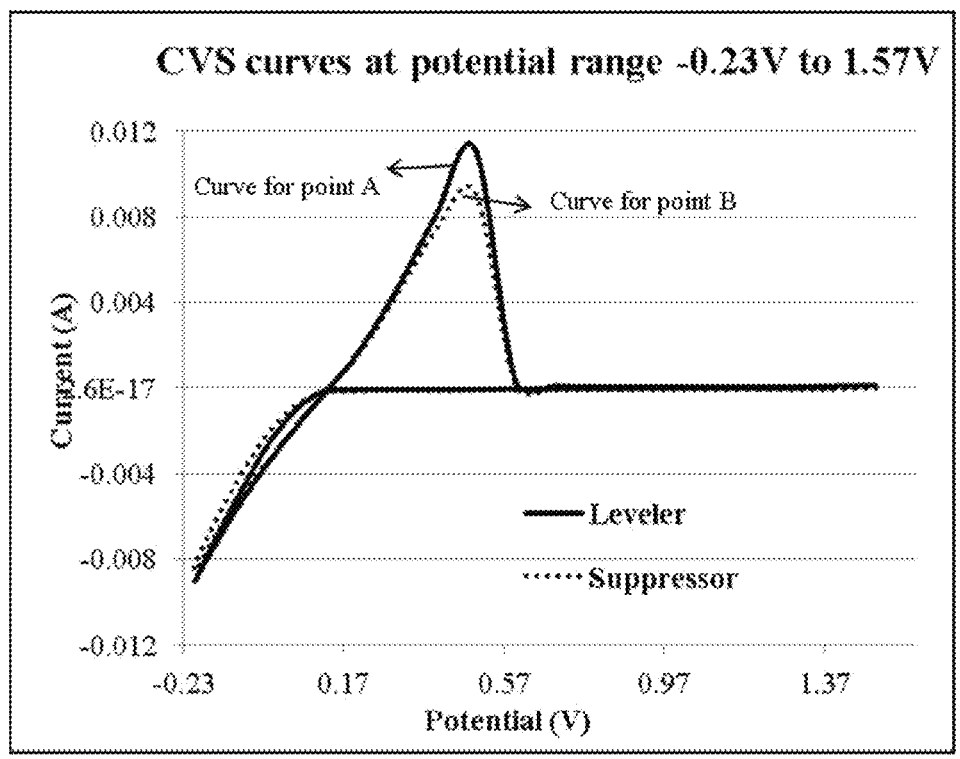
FIG. 5 shows cyclic voltammetric stripping (CVS) curves at potential range −0.23V to 1.57V for two supporting solutions with addition of suppressor solution and leveler solution respectively according to an embodiment of the presently claimed invention.
Figure 6:
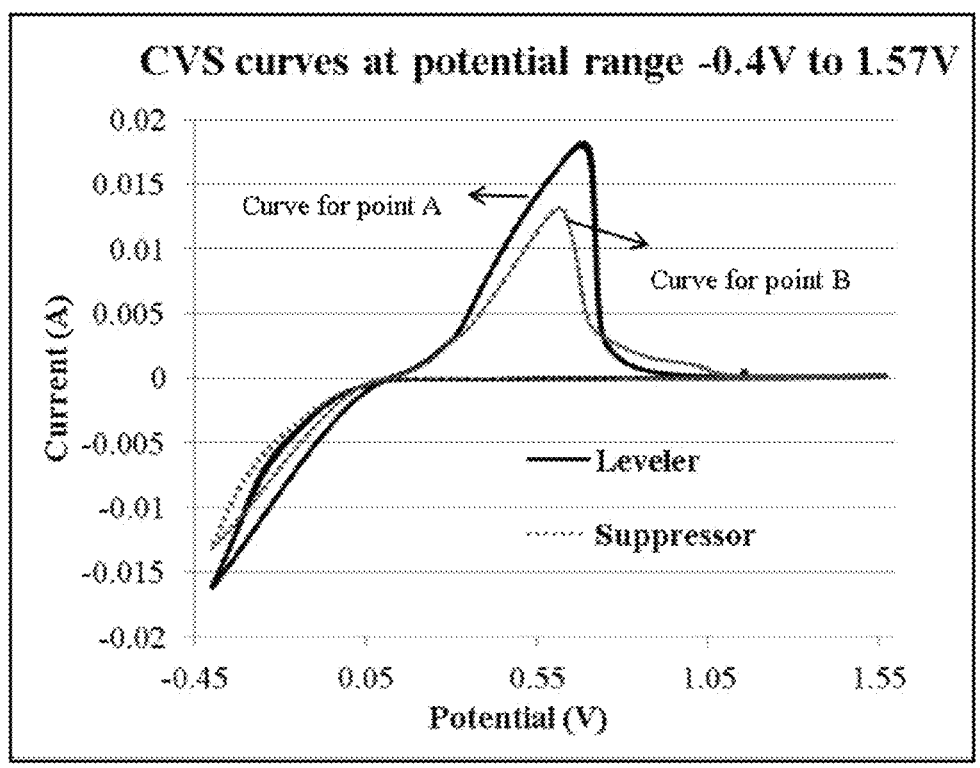
FIG. 6 shows cyclic voltammetric stripping curves at potential range −0.4V to 1.57V for two supporting solutions with addition of suppressor solution and leveler solution respectively according to an embodiment of the presently claimed invention.
Figure 7:
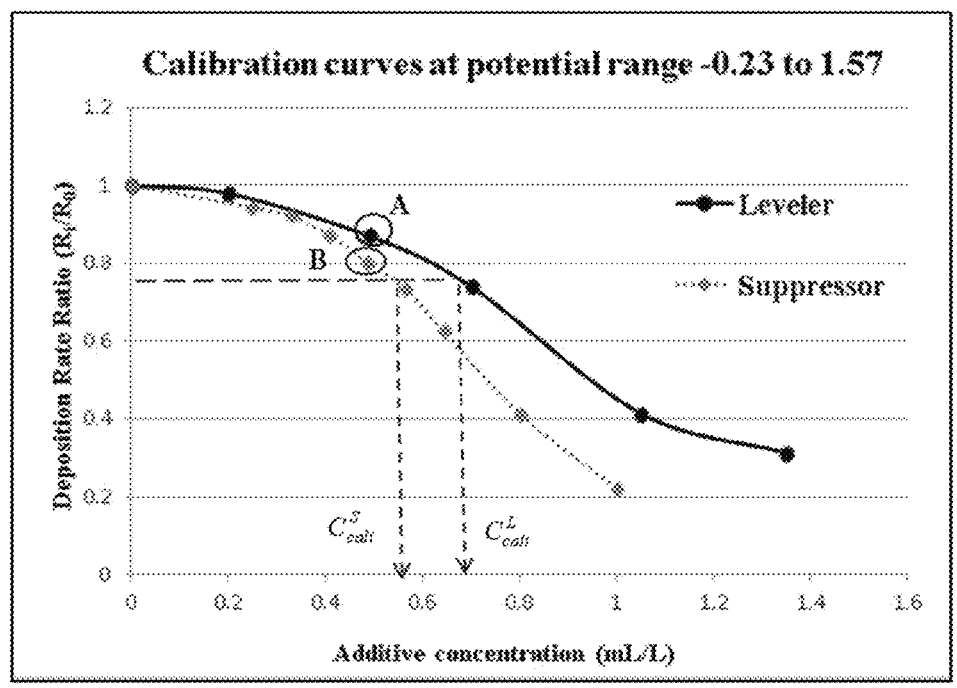
FIG. 7 shows calibration curves of deposition rate ratio ($R_i/R_o$) at the potential range of −0.23 to 1.57V for the supporting solutions with different suppressor concentrations, and different leveler concentrations respectively according to an embodiment of the presently claimed invention.

FIG. 5 shows cyclic voltammetric stripping curves at a potential range of −0.23V to 1.57V for two supporting solutions with a suppressor and a leveler respectively according to an embodiment of the presently claimed invention. The curve with solid line for leveler is used for determining point A as shown in FIG. 7. The curve with dotted line for suppressor is used for determining point B as shown in FIG. 7. Similarly, FIG. 6 shows cyclic voltammetric stripping curves at a potential range of −0.4V to 1.57V for two supporting solutions with the suppressor and the leveler respectively according to an embodiment of the presently claimed invention.

Figure 8:
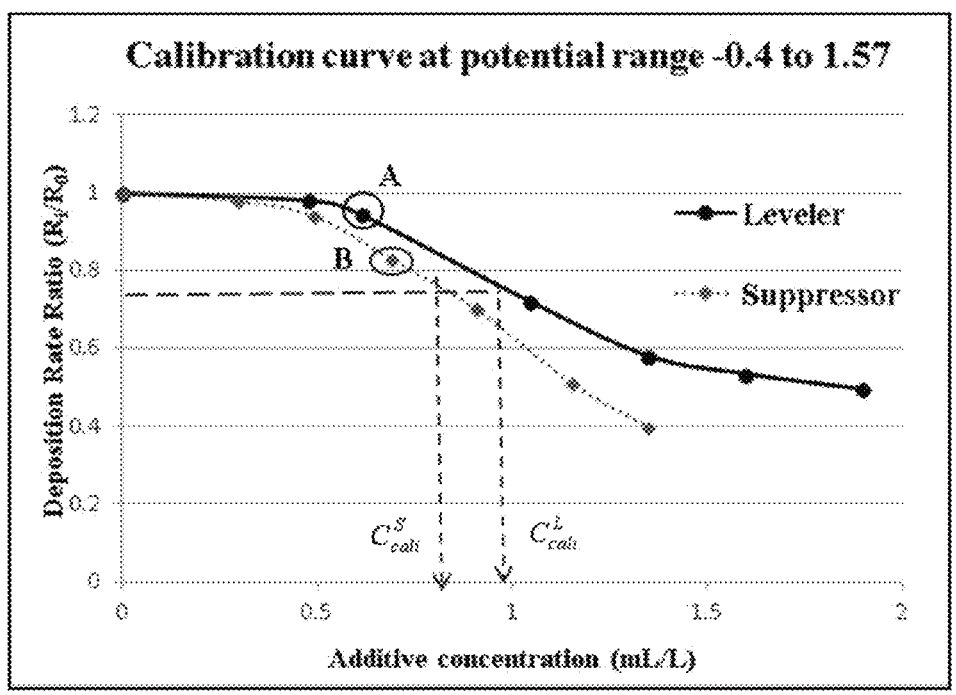
FIG. 8 shows calibration curves of deposition rate ratio ($R_i/R_o$) at the potential range of −0.4 to 1.57V for the supporting solutions with different suppressor concentrations, and different leveler concentrations respectively according to an embodiment of the presently claimed invention.

By calculating the charge required to strip the metal off the working electrode, the deposition rates of $R_0$ and $R_i$ are determined for further determining the deposition rate ratio as calculated by $R_i/R_0$. FIG. 7 shows calibration curves of the leveler and the suppressor respectively at the potential range of −0.23 to 1.57V according to an embodiment of the presently claimed invention. FIG. 8 shows calibration curves of the leveler and suppressor at the potential range of −0.4 to 1.57V according to an embodiment of the presently claimed invention.

Once acquiring the calibration curves, the calibrated concentrations of the leveler and suppressor are determined. As shown in FIG. 7-8, at the deposition rate ratio of 0.75, $C_{S,p1}^{cali}$ is determined as 0.5458 ml/L, and $C_{L,p1}^{cali}$ is determined as 0.6838 ml/L at the potential range of −0.23 to 1.57, while $C_{S,p2}^{cali}$ is determined as 0.8254 ml/L, and $C_{L,p2}^{cali}$ is determined as 0.9883 ml/L at the potential range of −0.4 to 1.57. By using the equations (4) and (5), the first inhibitor, α is calculated as 0.798, and the second inhibitor, β is calculated as 0.8352.

Figure 9:
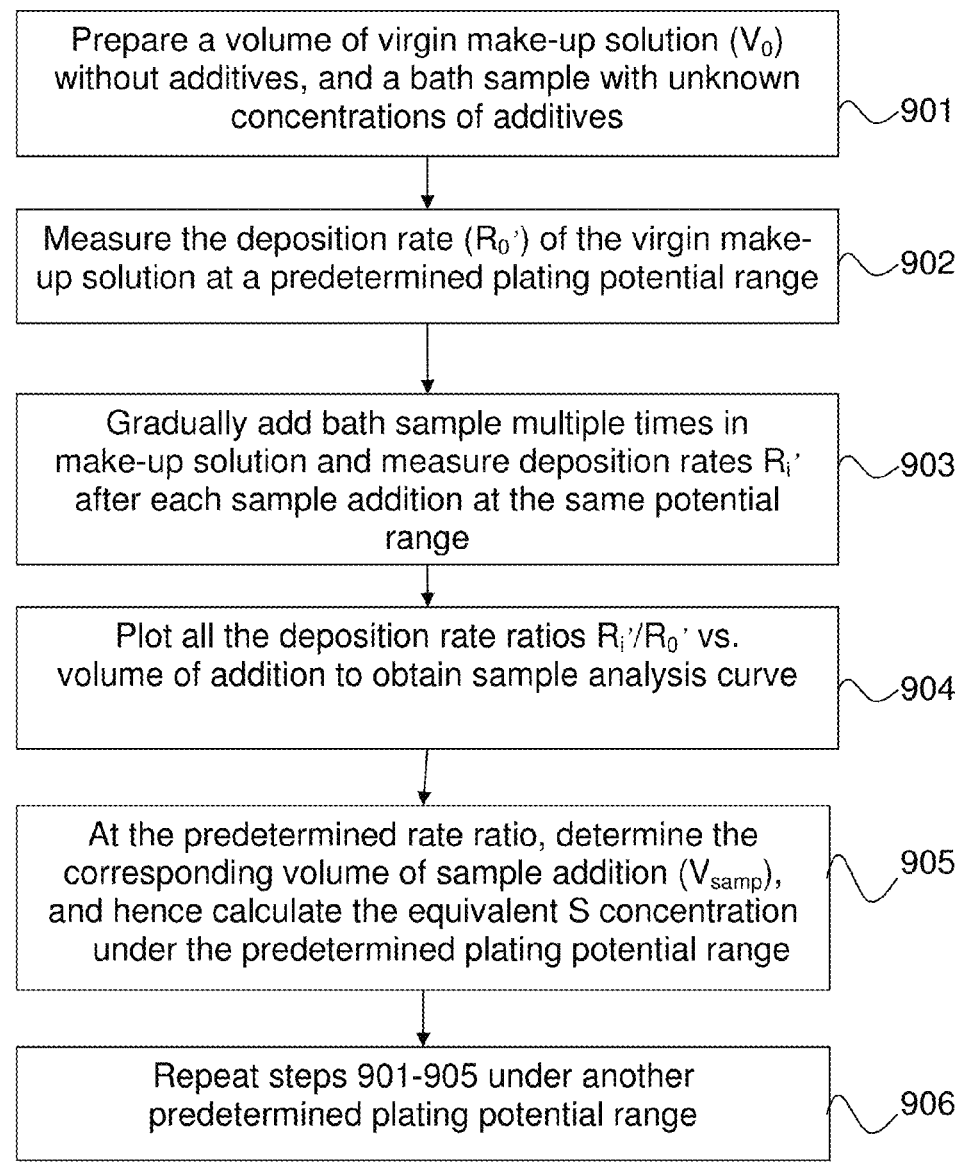
FIG. 9 shows a process flow chart illustrating the steps of determining two equivalent concentrations of a testing solution under two plating potential ranges according to one embodiment of the presently claimed invention.

FIG. 9 shows a process flow chart illustrating the steps of determining the two equivalent suppressor concentrations of a testing solution under two plating potential ranges according to one embodiment of the presently claimed invention. In step 901, a volume of virgin make-up solution ($V_0$) without additives, and a bath sample with unknown concentrations of the additives are prepared. In step 902, the deposition rate ($R_0'$) of the virgin make-up solution at the predetermined plating potential range is determined. In step 903, the bath sample is gradually added into the virgin make-up solution in multiple times to form multiple testing solutions, and various deposition rates $R_i'$ of the testing solutions having different volumes of bath sample after each addition of the bath sample at the same potential range are measured. In step 904, all the deposition rate ratios, calculated by $R_i'/R_0'$, are plotted versus volume of addition to obtain a sample analysis curve at the predetermined plating potential range. In step 905, at the predetermined deposition rate ratio, the corresponding volume of sample addition ($V_{samp}$) is determined based on the sample analysis curve, and hence the equivalent suppressor concentration is determined under the predetermined plating potential range. In step 906, steps 901-905 are repeated under another predetermined plating potential range for determining another equivalent suppressor concentration.

Accordingly, the equivalent suppressor concentrations at the first and the second plating potential ranges, $\gamma_{p1}$ and $\gamma_{p2}$ are calculated as follows:

$$\gamma_{p1} = C_{S,p1}^{cali} \frac{(V_0 + V_{samp,p1})}{V_{samp,p1}} \qquad (7)$$

$$\gamma_{p2} = C_{S,p2}^{cali} \frac{(V_0 + V_{samp,p2})}{V_{samp,p2}} \qquad (8)$$

where $V_{samp,p1}$ and $V_{samp,p2}$ are the volume of sample addition at the first and the second potential ranges.

Figure 10:
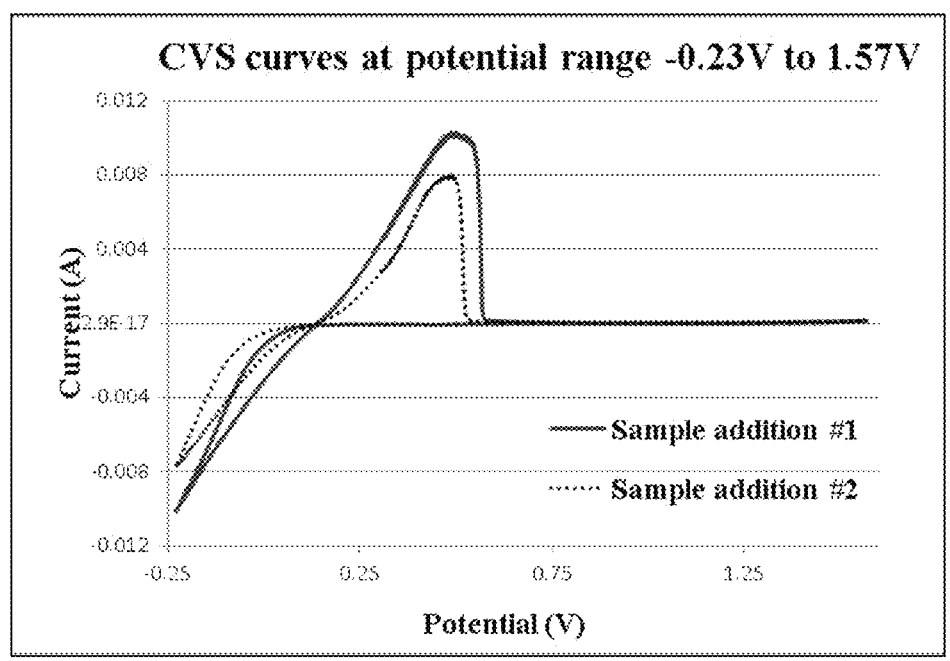
FIG. 10 shows cyclic voltammetric stripping curves at potential range −0.23V to 1.57V for two plating bath sample additions with unknown concentrations of additives according to an embodiment of the presently claimed invention.
Figure 11:
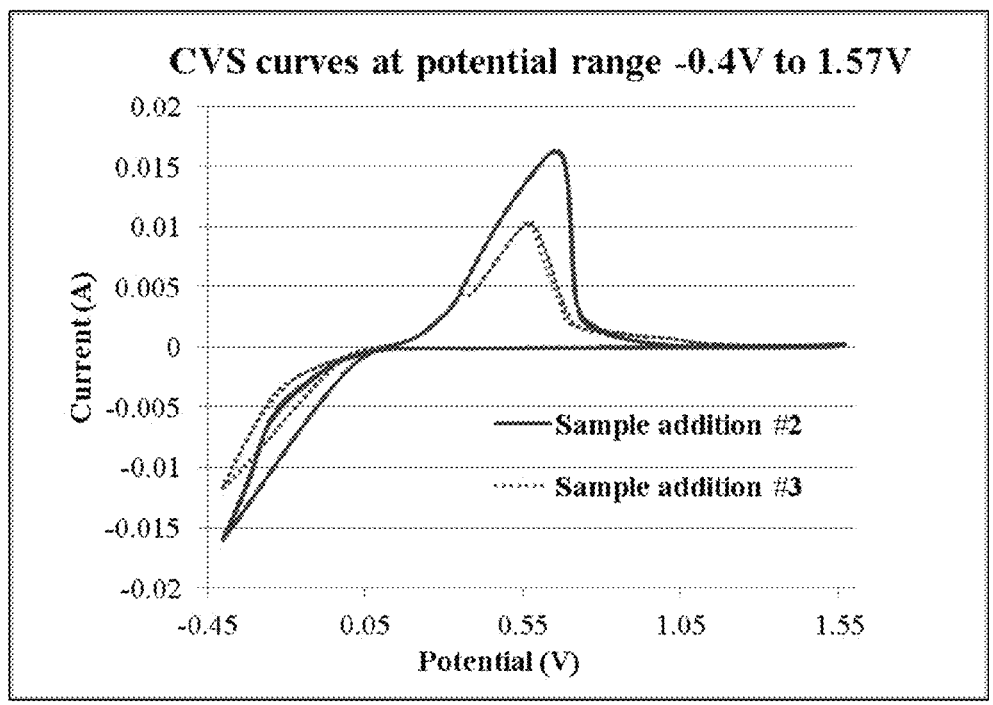
FIG. 11 shows cyclic voltammetric stripping curves at potential range −0.4V to 1.57V for two plating bath sample additions with unknown concentrations of additives according to an embodiment of the presently claimed invention.

FIG. 10 shows cyclic voltammetric stripping curves at potential range −0.23V to 1.57V for two plating bath sample additions with unknown concentrations of additives respectively according to an embodiment of the presently claimed invention. The curve with solid line is used for determining the point at sample addition #1 in FIG. 12. The curve with dotted line is used for determining the point at sample addition #2 in FIG. 12. Similarly, FIG. 11 shows cyclic voltammetric stripping curves at potential range −0.4V to 1.57V for two plating bath sample additions with unknown concentrations of additives respectively according to an embodiment of the presently claimed invention.

Figure 12:
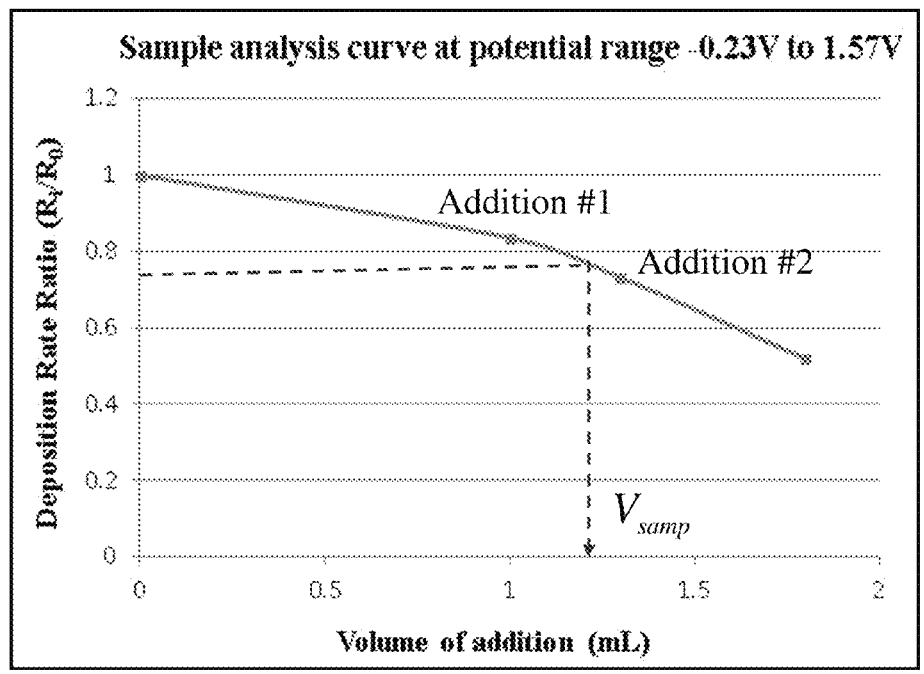
FIG. 12 shows sample analysis curves with deposition rate ratio versus volume of plating bath sample addition at potential range of −0.23 to 1.57V according to an embodiment of the presently claimed invention.
Figure 13:
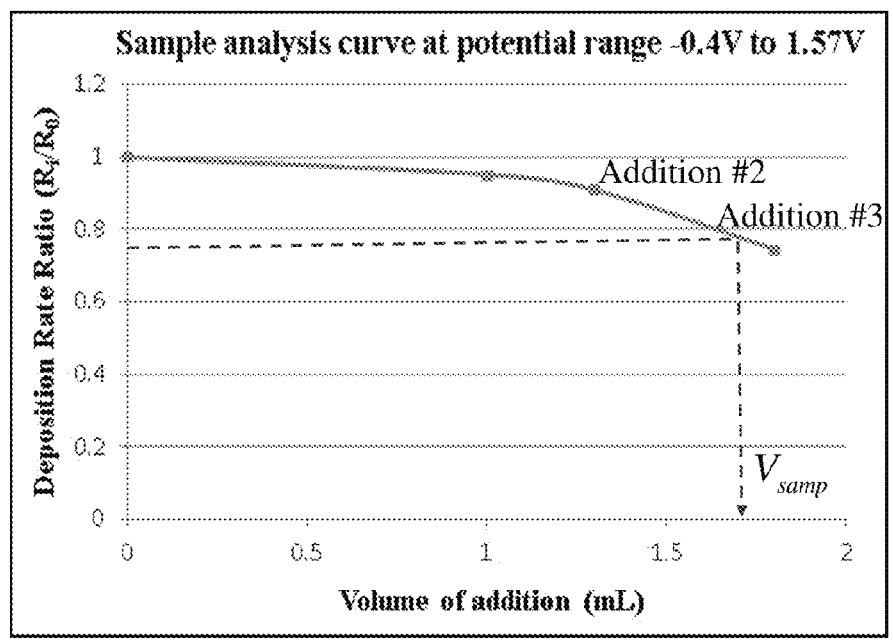
FIG. 13 shows sample analysis curves with deposition rate ratio versus volume of plating bath sample addition at potential range of −0.4 to 1.57V according to an embodiment of the presently claimed invention.

By calculating the charge required to strip the metal off the working electrode, the deposition rates of $R_0'$ and $R_i'$ are determined for further determining the deposition rate ratio, calculated by $R_i'/R_0'$. FIG. 12 shows sample analysis curves with deposition rate ratio versus volume of plating bath sample addition at potential range of −0.23 to 1.57V according to an embodiment of the presently claimed invention. FIG. 13 shows sample analysis curves with deposition rate ratio versus volume of plating bath sample addition at potential range of −0.4 to 1.57V according to an embodiment of the presently claimed invention.

Once acquiring the sample analysis curves, the volumes of sample addition are determined under different predetermined plating potential range. As shown in FIG. 12-13, at the deposition rate ratio of 0.75, $V_{samp,p1}$ is determined as 1.144 ml at the potential range of −0.23 to 1.57, and $V_{samp,p2}$ is determined as 1.744 ml at the potential range of −0.4 to 1.57. By using the equations (7) and (8), the equivalent suppressor concentrations for the predetermined plating potential ranges, $\gamma_{p1}$ and $\gamma_{p2}$ are calculated as 12.4724 ml/L and 12.6577 ml/L.

Consequently, by using the equations (3) and (4), $C_L$ is calculated as 8.4771 ml/L, and $C_S$ is calculated as 4.9946 ml/L.

According to an embodiment of the presently claimed invention, the suppressor concentrations and the leveler concentrations determined by the method of present invention are shown in the Table 2 and 3 respectively:

TABLE 2

| Sample | Actual S (ml/L) | Meas. S (ml/L) | Err. S |
|---|---|---|---|
| 1 | 8 | 8.4771 | 5.96% |
| 2 | 5 | 4.8853 | −2.29% |
| 3 | 10 | 9.8446 | −1.54% |

TABLE 3

| Sample | Actual L (ml/L) | Meas. L (ml/L) | Err. L |
|---|---|---|---|
| 1 | 5 | 4.9946 | −0.11% |
| 2 | 3 | 3.1727 | 5.74% |
| 3 | 6 | 6.2107 | 3.51% |

As shown in Table 2 and 3, when comparing the actual inhibitor concentration (obtained by the method of present invention) with the measured inhibitor concentration during production, the largest error generated by the present invention is merely about 5%, which is substantially lower that that of the prior art with about 49% as shown in Table 1. Hence nearly 90% of the error regarding the inhibitor concentration is reduced by the method of the present invention.

Accordingly, apart from using the cyclic voltammetric stripping to provide different plating potential ranges, other electrochemical analysis techniques, such as cyclic pulse voltammetric stripping, chronoamperometry, and chronopotentiometry, are applicable to apply electrical load conditions utilized for determining deposition rates. Different electrochemical analysis techniques have different loading modes. For example, the chronoamperometry provides plating current.

Accordingly, the present invention is not limited to analyzing two inhibitors simultaneously in an electroplating bath. Additive concentrations of more than two inhibitors can be effectively determined by the present invention.

According to an embodiment of the presently claimed invention, there are three inhibitors in a plating bath. The concentrations of the three inhibitors are calculated as follows:

$$C_S + \alpha_{ls}C_L + \alpha_{zs}C_Z = \gamma_{p1} \tag{9}$$

$$C_S + \beta_{ls}C_L + \beta_{zs}C_Z = \gamma_{p2} \tag{10}$$

$$C_S + \lambda_{ls}C_L + \lambda_{zs}C_Z = \gamma_{p3} \tag{11}$$

where $C_S$, $C_L$, $C_Z$ are concentrations for three inhibitors, S, L and Z respectively; $\alpha_{ls}$, $\alpha_{zs}$ are inhibition factors of L and Z relative to S under the first potential range respectively; $\beta_{ls}$, $\beta_{zs}$ are inhibition factors of L and Z relative to S under the second potential range respectively; $\lambda_{ls}$, $\lambda_{zs}$ are inhibition factors of L and Z relative to S under the third potential range respectively; and $\gamma_{p1}$, $\gamma_{p2}$, $\gamma_{p3}$ are equivalent concentrations of inhibitor S under the three different potential ranges respectively.

Hence, there are $$C_L = \frac{(\beta_{zs} - \lambda_{zs})(\gamma_{p1} - \gamma_{p2}) - (\alpha_{zs} - \beta_{zs})(\gamma_{p2} - \gamma_{p3})}{(\beta_{zs} - \lambda_{zs})(\alpha_{ls} - \beta_{ls}) - (\alpha_{zs} - \beta_{zs})(\beta_{ls} - \lambda_{ls})} \tag{12}$$

$$C_Z = \frac{(\beta_{ls} - \lambda_{ls})(\gamma_{p1} - \gamma_{p2}) - (\alpha_{ls} - \beta_{ls})(\gamma_{p2} - \gamma_{p3})}{(\beta_{ls} - \lambda_{ls})(\alpha_{zs} - \beta_{zs}) - (\alpha_{ls} - \beta_{ls})(\beta_{zs} - \lambda_{zs})} \tag{13}$$

$$C_S = \gamma_{p1} - \alpha_{ls}C_L - \alpha_{zs}C_Z \tag{14}$$

The embodiments disclosed herein may be implemented using general purpose or specialized computing devices, computer processors, or electronic circuitries including but not limited to digital signal processors (DSP), application specific integrated circuits (ASIC), field programmable gate arrays (FPGA), and other programmable logic devices configured or programmed according to the teachings of the present disclosure. Computer instructions or software codes running in the general purpose or specialized computing devices, computer processors, or programmable logic devices can readily be prepared by practitioners skilled in the software or electronic art based on the teachings of the present disclosure.

In some embodiments, the present invention includes computer storage media having computer instructions or software codes stored therein which can be used to program computers or microprocessors to perform any of the processes of the present invention. The storage media can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A method for determining additive concentrations of a first and a second inhibitors in a plating bath, comprising:
   determining a first and a second inhibition factors of the first and the second inhibitors by applying a first and a second electrical load conditions respectively on a first and a second supporting solutions;
   determining equivalent suppressor concentrations of a testing solution under the first and the second electrical load conditions respectively, wherein the testing solution comprises a virgin make-up solution and a portion of the plating bath, and the virgin make-up solution is an electrolyte solution comprising substances of the plating path except the first and the second inhibitors; and determining the additive concentrations of the first and the second inhibitors in the plating bath based on the first and the second inhibition factors and the equivalent suppressor concentrations of the testing solution under the first and the second electrical load conditions;

wherein the step of determining the first and second inhibitions factors further comprising the steps of:

(a) providing a standard solution of the first inhibitor, having a known amount of the first inhibitor;

(b) providing the virgin make-up solution;

(c) measuring an original deposition rate ($R_0$) of the virgin make-up solution under the first electrical load condition;

(d) adding a first volume of the standard solution of the first inhibitor into the virgin make-up solution to form the first supporting solution comprising the first volume of the standard solution of the first inhibitor;

(e) measuring a first deposition rate ($R_1$) of the first supporting solution comprising the first volume of the standard solution of the first inhibitor under the first electrical load condition to determine a first deposition rate ratio calculated by $R_1/R_0$;

(f) repeating the steps (d)-(e) by adding another volume of the standard solution of the first inhibitor to the virgin make-up solution to determine another deposition rate ratio till obtaining a calibration curve of the first inhibitor;

(g) repeating the steps (a)-(f) by using a standard solution of the second inhibitor to obtain a calibration curve of the second inhibitor;

(h) determining a calibrated concentration of the first inhibitor ($C_{1.cali.p1}$) and a calibrated concentration of the second inhibitor ($C_{2.cali.p1}$) for the first electrical load condition at a predetermined value of the deposition rate ratio based on the calibration curves of the first inhibitor and the second inhibitor;

(i) repeating the steps (a)-(g) under the second electrical load condition, and determining a calibrated concentration of the first inhibitor ($C_{1.cali.p2}$) and a calibrated concentration of the second inhibitor ($C_{2.cali.p2}$) for the second electrical load condition at the predetermined value of the deposition rate ratio; and (j) determining the first inhibition factor ($f_1$) for the first electrical load condition by $C_{1.cali.p1}/C_{2.cali.p1}$, and the second inhibition factor ($f_2$) for the second electrical load condition by $C_{1.cali.p2}/C_{2.cali.p2}$;

wherein the step of determining the equivalent suppressor concentrations of the testing solution further comprises steps of:

(a) providing a volume of the virgin mark-up solution ($V_0$);

(b) measuring an original deposition rate of the volume of the virgin make-up solution ($R_0'$) under the first electrical load condition;

(c) adding a first volume of the plating bath into the virgin make-up solution to form the testing solution comprising the first volume of the plating bath;

(d) measuring a first deposition rate ($R_1'$) of the testing solution comprising the first volume of the plating bath under the first electrical load condition to determine a first deposition rate ratio calculated by $R_1'/R_0$;

(e) repeating the steps (c)-(d) by adding another volume of the plating bath to determine another deposition rate ratio till obtaining an analysis curve of the plating bath solution;

(f) determining a volume of plating bath sample addition for the first electrical load condition at the predetermined value of the deposition rate ratio ($V_{samp.p1}$);

(g) repeating steps (a)-(e) under the second electrical load condition and determining a volume of plating bath sample addition for the second electrical load condition at the predetermined value of the deposition rate ratio ($V_{samp.p2}$); and (h) determining the equivalent suppressor concentrations of the plating bath solution for the first electrical load condition ($e_1$) with $C_{1.cali.p1}*(V_0+V_{samp.p1})/V_{samp.p1}$, and for the second electrical load condition ($e_2$) with $C_{1.cali.p2}*(V_0+V_{samp.p2})/V_{samp.p2}$; and wherein the additive concentration of the first inhibitor ($C_1$) and the additive concentration of the second inhibitor ($C_2$) in the plating bath are determined as follows:

$$C_1=(f_1 e_2 - f_2 e_1)/(f_1-f_2)$$

$$C_2=(e_1-e_2)/(f_1-f_2).$$

2. The method of claim 1, wherein the first and the second electrical load conditions are applied by cyclic voltammetric stripping, cyclic pulse voltammetric stripping, chronoamperometry, or chronopotentiometry.

3. The method of claim 2, wherein the cyclic voltammetric stripping provides plating potential for the electrical load conditions, and the chronoamperometry provides plating current for the electrical load conditions.

4. The method of claim 1, wherein the first inhibitor is a leveler, and the second inhibitor is a suppressor.

5. A method for determining additive concentrations of at least two inhibitors in a plating bath, comprising:

determining at least two inhibition factors of the at least two inhibitors by applying at least two electrical load conditions on at least two supporting solutions respectively;

determining equivalent suppressor concentrations of a testing solution under the at least two electrical load conditions respectively, wherein the testing solution comprises a virgin make-up solution and a portion of the plating bath, and the virgin make-up solution is an electrolyte solution comprising substances of the plating bath except the at least two inhibitors; and determining the additive concentrations of the at least two inhibitors based on the at least two inhibition factors and the equivalent suppressor concentrations of the testing solution under the at least two electrical load conditions;

wherein the step of determining the at least two inhibition factors further comprises steps of:

(a) providing a first standard solution of a first inhibitor from the at least two inhibitors, having a known amount of the first inhibitor;

(b) providing the virgin make-up solution;

(c) measuring an original deposition rate ($R_0$) of the virgin make-up solution under a first electrical load condition from one of the at least two electrical load conditions;

(d) adding a first volume of the first standard solution of the first inhibitor into the virgin make-up solution to form the supporting solution comprising the first volume of the first standard solution of the first inhibitor;

(e) measuring a first deposition rate ($R_1$) of the supporting solution comprising the first volume of the first standard solution of the first inhibitor under the first electrical load condition to determine a first deposition rate ratio calculated by $R1/R_0$;

(f) repeating the steps (d)-(e) by adding another volume of the first standard solution of the first inhibitor to determine another deposition rate ratio till obtaining a calibration curve of the first inhibitor;

(g) repeating the steps (a)-(f) by using another standard solution of another inhibitor from the at least two inhibitors to obtain another calibration curve of the another inhibitor till obtaining all of the calibration curves of each of the at least two inhibitors;

(h) determining calibrated concentrations of the at least two inhibitors for the first electrical load condition at a predetermined value of the deposition rate ratio based on the calibration curves of each of the at least two inhibitors;

(i) repeating the steps (a)-(g) under another electrical load condition from the at least two electrical load conditions and determining another calibrated concentrations of another inhibitor for another electrical load condition at the predetermined value of the deposition rate ratio till obtaining all of the calibrated concentrations of each of the at least two inhibitors for each of the at least two electrical load conditions; and (i) determining the at least two inhibition factors for each of the at least two electrical load conditions based on all of the calibrated concentrations;

wherein the step of determining the equivalent suppressor concentrations of the testing solution further comprises steps of:

(a) providing a volume of the virgin mark-up solution;

(b) measuring an original deposition rate of the volume of the virgin mark-up solution ($R_0'$) under the first electrical load condition;

(c) adding a first volume of the plating bath into the virgin mark-up solution to form the testing solution comprising the first volume of the plating bath;

(d) measuring a first deposition rate ($R_1'$) of the testing solution comprising the first volume of the plating bath under the first electrical load condition to determine a first deposition rate ratio calculated by $R_1'/R_0'$;

(e) repeating the steps (c)-(d) by adding another volume of the plating bath to determine another deposition rate ratio till obtaining an analysis curve of the plating bath solution for the first electrical load condition;

(f) determining a volume of plating bath sample addition at the predetermined value of the deposition rate ratio for the first electrical load condition;

(g) repeating steps (a)-(e) under another electrical load condition from the at least two electrical load conditions and determining another volume of plating bath sample addition for another electrical load condition at the predetermined value of the deposition rate ratio till obtaining all of the volumes of plating bath sample addition for each of the at least two electrical load conditions; and (h) determining the equivalent suppressor concentrations of the plating bath solution based on the volumes of plating bath sample addition of each of the at least two electrical load conditions, and the calibrated concentrations of each of the at least two electrical load conditions; and wherein the at least two inhibitors comprises three inhibitors including the first inhibitor (S), a second inhibitor (L), and a third inhibitor (Z), and concentrations for S, L, and Z respectively are calculated as follow:

$$C_L = \frac{(\beta_{zs} - \lambda_{zs})(\gamma_{p1} - \gamma_{p2}) - (\alpha_{zs} - \beta_{zs})(\gamma_{p2} - \gamma_{p3})}{(\beta_{zs} - \lambda_{zs})(\alpha_{ls} - \beta_{ls}) - (\alpha_{zs} - \beta_{zs})(\beta_{ls} - \lambda_{ls})}$$

$$C_Z = \frac{(\beta_{ls} - \lambda_{ls})(\gamma_{p1} - \gamma_{p2}) - (\alpha_{ls} - \beta_{ls})(\gamma_{p2} - \lambda_{p3})}{(\beta_{ls} - \lambda_{ls})(\alpha_{zs} - \beta_{zs}) - (\alpha_{ls} - \beta_{ls})(\beta_{zs} - \lambda_{zs})}$$

$$C_S = \gamma_{p1} - \alpha_{ls}C_L - \alpha_{zs}C_Z$$

where $C_S$, $C_L$, $C_Z$ are concentrations for the three inhibitors, S, L and Z respectively: $\alpha_{ls}$, $\alpha_{zs}$, are inhibition factors of L and Z relative to S under the first electrical load condition respectively: $\beta_{ls}$, $\beta_{zs}$, are inhibition factors of L and Z relative to S under a second electrical load condition respectively: $\lambda_{ls}$, $\lambda_{zs}$ are inhibition factors of L and Z relative to S under a third electrical load condition respectively; and $\gamma_{p1}$, $\gamma_{p2}$, $\gamma_{p3}$ are equivalent concentrations under the first, the second and the third electrical load conditions respectively.

6. The method of claim 5, wherein the at least two electrical load conditions are applied by cyclic voltammetric stripping, cyclic pulse voltammetric stripping, chronoamperometry, and chronopotentiometry.

7. The method of claim 6, wherein the cyclic voltammetric stripping provides plating potential for the electrical load conditions, and the chronoamperometry provides plating current for the electrical load conditions.

8. The method of claim 5, wherein the at least two inhibitors comprises at least one leveler, or at least one suppressor.

* * * * *